United States Patent
Fehr et al.

(10) Patent No.: US 12,324,570 B2
(45) Date of Patent: Jun. 10, 2025

(54) APPARATUS FOR THE DETECTION OF CARBON DIOXIDE

(71) Applicant: Radiometer Basel AG, Basel (CH)

(72) Inventors: Jean-Nöel Fehr, Brønshøj (DK); Jean-Christophe Roulet, Brønshøj (DK); Patrizia Weber, Brønshøj (DK); Julien Finci, Brønshøj (DK); Lukas Scherer, Brønshøj (DK)

(73) Assignee: RADIOMETER BASEL AG, Basel (CH)

( * ) Notice: Subject to any disclaimer, the term of this patent is extended or adjusted under 35 U.S.C. 154(b) by 1081 days.

(21) Appl. No.: 16/954,721

(22) PCT Filed: Dec. 14, 2018

(86) PCT No.: PCT/EP2018/084959
§ 371 (c)(1),
(2) Date: Jun. 17, 2020

(87) PCT Pub. No.: WO2019/121395
PCT Pub. Date: Jun. 27, 2019

(65) Prior Publication Data
US 2021/0085295 A1  Mar. 25, 2021

(30) Foreign Application Priority Data
Dec. 22, 2017 (DK) .............. PA 2017 00742

(51) Int. Cl.
*A61B 10/00* (2006.01)
*A61B 5/00* (2006.01)
*A61B 5/145* (2006.01)
*G01N 33/497* (2006.01)

(52) U.S. Cl.
CPC .......... *A61B 10/00* (2013.01); *A61B 5/14542* (2013.01); *A61B 5/443* (2013.01); *G01N 33/497* (2013.01); *A61B 2010/0083* (2013.01)

(58) Field of Classification Search
CPC ..... A61B 10/00; A61B 5/14542; A61B 5/443; A61B 2010/0083; A61B 5/14552; A61B 5/14521; A61B 2562/04; A61B 5/0075; A61B 5/0836; G01N 33/497; A61M 2230/202
See application file for complete search history.

(56) References Cited

U.S. PATENT DOCUMENTS

| | | |
|---|---|---|
| 4,041,932 A | 8/1977 | Fostick |
| 5,630,413 A | 5/1997 | Thomas et al. |
| 2016/0029977 A1 | 2/2016 | Di Resta et al. |

FOREIGN PATENT DOCUMENTS

| | | |
|---|---|---|
| EP | 1 482 301 A | 12/2004 |
| GB | 2 442 980 A | 4/2008 |

(Continued)

OTHER PUBLICATIONS

International Search Report for International Application No. PCT/EP2018/084959, Mar. 14, 2019 (three pages).

(Continued)

*Primary Examiner* — Tse W Chen
*Assistant Examiner* — Evelyn Grace Park
(74) *Attorney, Agent, or Firm* — Frost Brown Todd LLC (57) ABSTRACT

The present invention relates to an apparatus (10) apparatus for the detection of carbon dioxide. It is described to place (210) a part of a housing in contact with a skin area of a patient. the part of the housing and a gas measuring chamber within the housing are configured such that gases diffusing through the skin area of the patient enter the gas measuring chamber. radiation is emitted (220) from a radiation source within the housing, wherein at least some of the radiation emitted by the radiation source enters the gas measuring chamber. The radiation entering the gas measuring chamber has wavelengths that extend over an absorption band of carbon dioxide and has wavelengths that extend over a region other than the absorption band of carbon dioxide. A (Continued)

radiation filter is positioned (230) relative to the gas measuring chamber such that an interaction radiation path is defined between the radiation source through the gas measuring chamber to the radiation filter. A first radiation detector is positioned (240) relative to the radiation filter such that a first detection radiation path is defined that is in addition to the interaction radiation path, and a second radiation detector is positioned relative to the radiation filter such that a second detection radiation path is defined that is in addition to the interaction radiation path. The radiation filter is configured such that radiation in the first detection radiation path has a wavelength that extends over the absorption band of carbon dioxide and with an intensity of radiation that extends over the region other than the absorption band being significantly less than that in the interaction radiation path. The radiation filter is also configured such that radiation in the second detection radiation path has a wavelength that extends over the region other than the absorption band of carbon dioxide and with an intensity of radiation that extends over the absorption band being significantly less than that in the interaction radiation path. a partial pressure of carbon dioxide is determined (250) in the skin of the patient using a signal from the first radiation detector and a signal from the second radiation detector.

20 Claims, 6 Drawing Sheets

(56) References Cited

FOREIGN PATENT DOCUMENTS

| JP | 2014-506488 A | 3/2014 | |
|---|---|---|---|
| JP | 2016-527505 | 9/2016 | |
| WO | WO 90/07106 | 6/1990 | |
| WO | WO 98/20324 | 5/1998 | |
| WO | WO 2012/101556 A1 | 8/2012 | |
| WO | WO-2016173877 A1 * | 11/2016 | ......... A61B 5/14551 |

OTHER PUBLICATIONS

Written Opinion of the International Searching Authority for International Application No. PCT/EP2018/084959 (six pages).

* cited by examiner

APPARATUS FOR THE DETECTION OF CARBON DIOXIDE

This application is a national stage filing under 35 U.S.C. § 371 of International Application No. PCT/EP2018/084959, filed on Dec. 14, 2018, which claims priority of Danish Patent Application No. PA 2017 00742, filed on Dec. 22, 2017. The contents of these applications are each incorporated herein by reference in their entirety.

FIELD OF THE INVENTION

The present invention relates to an apparatus for the detection of carbon dioxide, to a system for the detection of carbon dioxide, to a method for the detection of carbon dioxide, as well as to a computer program element and computer readable medium.

BACKGROUND OF THE INVENTION

The non-invasive measurement of the partial pressure of blood gases by means of an apparatus, such as a sensor, applied to the skin of a human or animal for measuring the partial pressure of the blood gases has been described in many publications as a useful tool in a number of clinical situations. Sensors for non-invasively measuring blood gases such as carbon dioxide ($CO_2$) and oxygen ($O_2$) are indispensable tools at Intensive Care Units (ICU) and Neonatal Intensive Care Units (NICU) because they provide reliable continuous monitoring of the respiratory function of the patient, human or animal, in a non-invasive way and with minimum amount of work for the hospital staff.

The trend within the field of cutaneous/transcutaneous blood gas sensors is generally to decrease the size of both sensors and monitors. One of the preferred sites for measuring the transcutaneous partial pressure of blood gases is the earlobe, since the skin of the earlobe is very thin. Furthermore, measuring the transcutaneous partial pressure of blood gases is often used on preterm neonates. Irrespective of whether the sensor is used on neonates or on adults it may be difficult to find a suitable flat area on the skin large enough to adequately accommodate a blood gas sensor. Thus the size of the sensor should be minimized.

Such sensors should be able to measure on a small sample surface, and the response time should be short. Since the required sensitivity of the sensor is required to be high due to the small changes of gas concentration, the signal strength should be as large as possible, e.g. no more than 60 seconds, thus available signal strengths should be as large as possible. In order to make a monitoring system as easy to use as possible, the monitoring system should also always be ready to use and drift-free during use. Such sensors should also be relatively inexpensive, and simple to assemble.

Commercially available products for cutaneous or transcutaneous measurement of the partial pressure of blood gases are usually electrochemical sensors. These electrochemical sensors have been known for decades to provide an accurate estimate of the partial pressure of blood gases in the skin of the human, from which the arterial partial pressure can be calculated, giving the medical staff at especially ICU, NICU, and sleep laboratories a clear indication of the patients respiratory function, without the need of taking a blood sample. Electrochemical sensors as described are known from e.g. U.S. Pat. No. 6,654,622 B1.

Although electrochemical sensors as known have proven to be indispensable tools at hospitals, they require frequent calibration, the signal may drift, which may cause problems for applications of longer duration, e.g. sleep monitoring, and the require frequent remembraning including adding an electrolyte solution. Hence, it has been a wish to develop another kind of apparatus not having these problems.

WO20081 10927 discloses an optical sensor using a tunable laser-diode technology, wherein the light beam propagates by single monomodal propagation in a sampling cell, before the light beam is received at a detector, producing an output signal reflecting the chemical substance of the sample.

WO2003023374 discloses an optical sensor using an evanescent field to penetrate into the skin to detect the chemical substance in the skin.

For both of the technologies in WO2003023374 and WO20081 10927, the light source is a laser mounted external to the sensor, transmitting light to the sensor via light guides. These systems have several disadvantages as backlight interferes within the laser cavity due to optical interferences on the light pathway, decreasing the sensitivity critically. Furthermore, these systems use a laser light source providing light at one single frequency, which may then be tuned for absorption by one gas, e.g. carbon dioxide, at either the keynote or one of its overtones. However lasers have several disadvantages. Lasers are costly and bulky compared to other light sources. Because of their size lasers were mounted in an external device and the light was transmitted via fiber optics to the sensor. Fiber optics cables are likely to break due to stress after some time of usage. Furthermore, although the laser is tuned to a specific wavelength, the laser drifts due to temperature changes, which has become a problem for the use in sleep monitoring, where the room temperature is lowered overnight, changing the wavelength of the light in the detector system. Hence a system using laser requires constant modulation monitoring to ensure that the laser supplies light at the intended wavelength.

WO2015010709 discloses an optical sensor for detection of $CO_2$ using an Infrared (IR) light source transmitting IR light through an Numerical Aperture (NA) converter and a wavelength filter into a measuring volume having several reflecting surfaces for in-creasing the signal path, to a detector detecting the amount of light coming through the measuring volume. A change in the light transmitted through the measuring volume is used for estimating the changes in the amount of $CO_2$ in the measuring volume. This is also known in optics as "non-imaging", i.e. the photodetectors are not used for creating an image of the sample in the measuring volume but instead detect changes within the measuring volume.

The term cutaneous in this context means a measurement of the situation in the epidermal layer of the patient, human or animal. The term transcutaneous is often referred to as a measurement wherein the situation beneath the epidermal layer is examined. A transcutaneous measurement is no different from a cutaneous measurement, except that the temperature is higher for transcutaneous measurements whereby the blood flow in the epidermal layer is increased, making the epidermal layer more arterial like, i.e. the epidermal layer behaves more like the layers beneath the epidermis. How much of a temperature increase is necessary to conduct a transcutaneous measurement depends on the skin of the patient. A neonate or preterm neonate has a very thin skin; hence a temperature of e.g. 40° C. may be enough to conduct a transcutaneous measurement of blood gases, whereas elderly people having a thicker skin layer, temperatures of 44° C., or 45° C. may be necessary to arterialize the epidermis. Within the context of this invention it is irrelevant whether the purpose of the measurement is to examine the situation in the epidermis or beneath the epidermis. Hence whether the term cutaneous or transcutaneous is used describing the invention, either term covers that a measurement of the blood gas partial pressure is measured using a sensor applied to the skin of a human.

SUMMARY OF THE INVENTION

It would be advantageous to have an improved sensor system and associated method for the detection of carbon dioxide.

The object of the present invention is solved with the subject matter of the independent claims, wherein further embodiments are incorporated in the dependent claims. It should be noted that the following described aspects and examples of the invention apply also for the apparatus for the detection of carbon dioxide, the system for the detection of carbon dioxide, the method for the detection of carbon dioxide, and for the computer program element and computer readable medium.

According to a first aspect, there is provided an apparatus for the detection of carbon dioxide, comprising:
a housing;
a gas measuring chamber;
a radiation source;
a first radiation detector;
a second radiation detector; and
a radiation filter.

The gas measuring chamber, the radiation source, the first radiation detector, the second radiation detector, and the radiation filter are housed within the housing. A part of the housing is configured to be placed in contact with a skin area of a patient. The part of the housing and the gas measuring chamber are configured such that gases diffusing through the skin area of the patient enter the gas measuring chamber. The gas measuring chamber and radiation source are configured such that at least some of the radiation emitted by the radiation source enters the gas measuring chamber. The radiation entering the gas measuring chamber has wavelengths that extend over an absorption band of carbon dioxide and has wavelengths that extend over a region other than the absorption band of carbon dioxide. The radiation filter is positioned relative to the gas measuring chamber such that an interaction radiation path is defined between the radiation source through the gas measuring chamber to the radiation filter. The first radiation detector is positioned relative to the radiation filter such that a first detection radiation path is defined that is in addition to the interaction radiation path. The second radiation detector is positioned relative to the radiation filter such that a second detection radiation path is defined that is in addition to the interaction radiation path. The radiation filter is configured such that radiation in the first detection radiation path has wavelengths that extend over the absorption band of carbon dioxide and with an intensity of radiation that extends over the region other than the absorption band being significantly less than an intensity of radiation that extends over the region other than the absorption band in the interaction radiation path. The radiation filter is configured such that radiation in the second detection radiation path has wavelengths that extend over the region other than the absorption band of carbon dioxide and with an intensity of radiation that extends over the absorption band being significantly less than an intensity of radiation that extends over the absorption band in the interaction radiation path. Signals from the first and second radiation detectors are useable to determine a partial pressure of carbon dioxide in the skin of the patient.

In other words, a non-invasive carbon dioxide measuring apparatus uses an interference filter to separate radiation over a carbon dioxide absorption band from radiation that is not over that band. Then, all the radiation over the absorption band can be directed to a first detector with minimal radiation over this wavelength range going to a second detector. However, the second detector can detect all the radiation over a different wavelength range that can suffer from minimal absorption from carbon dioxide, with the first detector not detecting radiation over this wavelength range. In this manner, each detector is provided with a maximum possible signal, with minimal background signal present, with the first detector detecting the absorption of carbon dioxide with the second detector acting as a reference signal detector.

Thus, the filter can be a pass-band filter that transmits the wavelengths over the absorption band of carbon dioxide and reflects other wavelengths, or the filter can reflect the wavelengths over the absorption band of carbon dioxide and transmit other wavelengths.

Thus, a gas sensor is provided with minimal components, leading to a reduction in size, and at the same time increased signal intensities are provided leading to increased signal to noise and enabling detection times to be reduced, and assembly is facilitated because manufacturing and assembly tolerances are not severe, leading to an overall sensor apparatus that is very compact, exhibits high signal intensities, is simple to assemble, and is not overly expensive.

In an example, the radiation filter is configured such that the second detection radiation path comprises radiation transmitted through the radiation filter, and the first detection radiation path comprises radiation reflected from the radiation filter.

In other words radiation reflected from the radiation filter has radiation over an absorption band of carbon dioxide and is used to detect the presence of gaseous carbon dioxide. At the same time, radiation transmitted by the filter has radiation over a region other than the absorption band of carbon dioxide, and can be used as a reference signal.

To put this another way, the apparatus uses a filter that reflects over an absorption band of a gas to be detected and transmits over other wavelengths as a reference channel.

In an example, the radiation filter comprises a transmission passband centred at a wavelength where minimal gaseous absorption occurs.

In this way, radiation transmitted through the radiation filter that acts as a reference signal is centred at a region of low absorption, and is not perturbed by the presence of gases in the measuring chamber.

In an example, the centre wavelength of the transmission passband is 3.91 micrometers (μm). Other passband wavelengths can be used, especially when detecting other gases. By configuring the radiation filter in this manner the centre passband transmission wavelength is away from parasitic absorption lines, such as those for $H_2O$ or $N_2O$.

In an example, a full width half maximum of the transmission passband is 90 nanometers (nm). Other FWHM can be used.

Thus, the radiation filter is configured as a narrowband transmission filter, with a centre transmission wavelength and FWHM that maximises the signal that can be acquired, and at the same time ensures that radiation extending over parasitic absorption lines, such as for $H_2O$ or $N_2O$ is not detected.

In an example, the apparatus comprises a second radiation filter. The second radiation filter is configured such that the first detection radiation path comprises radiation transmitted through the second radiation filter.

In other words, a first radiation filter transmits radiation that is used for a reference signal and the first radiation filter reflects radiation that is used to detect for the presence of carbon dioxide. Thus a cost effective first filter can be used to transmit radiation to optimise detection of the reference signal and provide a reflectance signal to be used for the detection of carbon dioxide where this reflected signal may not be optimised. However, a second radiation filter can then be used in this detection channel, that for example has a narrow passband centred at an absorption band of carbon dioxide. This combination then provides for increased signal to noise and increased dynamic range, because all the available photons are detected in each channel. This is because each channel can in effect have a filter that only allows the required photons to propagate to the respective detectors, and extraneous photons that do not either provide the required reference signal or required carbon dioxide detection signal are excluded from the respective channels.

To put this another way, a first filter can be a narrow pass band transmission filter centred on a part of the spectrum where there is little absorption, providing for a reference channel that accounts for example for drift in the source output. This filter can then have a broadband reflectance that extends over an absorption band of carbon dioxide. Then a second radiation filter in used in this second detection channel, that is again a narrow passband transmission filter, that now is centred on an absorption band of carbon dioxide.

In this manner, the radiation in the first and second detection radiation paths can be controlled separately to provide for optimal carbon dioxide detection along with an optimal reference signal determination. This can be done in a manner that maximises the radiation of interest to be detected, and excluding unwanted radiation, thereby maximising signal to noise and dynamic range. By using two filters, gas detection selectivity is improved.

In an example, the second radiation filter comprises a transmission passband that extends over the absorption band of carbon dioxide.

In an example, the centre wavelength of the transmission passband is 4.26 micrometers (μm). Other passband wavelengths can be used when detecting other gases.

In an example, a full width half maximum of the transmission passband is 180 nanometers (nm). Other FWHM can be used.

In an example, the radiation filter acts as a gaseous seal to the gas measuring chamber.

In an example, the second radiation filter acts as a gaseous seal to the gas measuring chamber.

According to a second aspect, there is provided a system for the detection of carbon dioxide, comprising:
an apparatus for the detection of carbon dioxide according to the first aspect;
a processing unit; and
an output unit.

The processing unit is configured to control the apparatus, and is configured to control the output unit. The apparatus is configured to provide the processing unit with the signal from the first radiation detector and the signal from the second radiation detector. The processing unit is configured to calculate the partial pressure of carbon dioxide in the skin of the patient, the calculation comprising utilization of the signal from the first radiation detector and the signal from the second radiation detector. The output unit is configured to output data representative of the partial pressure of carbon dioxide.

In an example, the calculation comprises a difference between the signal from the second radiation detector and the signal from the first radiation detector.

According to a third aspect, there is provided method for the detection of carbon dioxide, comprising:
a) placing a part of a housing in contact with a skin area of a patient; wherein, the part of the housing and a gas measuring chamber within the housing are configured such that gases diffusing through the skin area of the patient enter the gas measuring chamber;
b) emitting radiation from a radiation source within the housing, wherein at least some of the radiation emitted by the radiation source enters the gas measuring chamber, and wherein the radiation entering the gas measuring chamber has wavelengths that extend over an absorption band of carbon dioxide and has wavelengths that extend over a region other than the absorption band of carbon dioxide;
c) positioning a radiation filter relative to the gas measuring chamber such that an interaction radiation path is defined between the radiation source through the gas measuring chamber to the radiation filter;
d) positioning a first radiation detector relative to the radiation filter such that a first detection radiation path is defined that is in addition to the interaction radiation path; and wherein a second radiation detector is positioned relative to the radiation filter such that a second detection radiation path is defined that is in addition to the interaction radiation path; wherein the radiation filter is configured such that radiation in the first detection radiation path has a wavelength that extends over the absorption band of carbon dioxide and with an intensity of radiation that extends over the region other than the absorption band being significantly less than that in the interaction radiation path; and wherein the radiation filter is configured such that radiation in the second detection radiation path has a wavelength that extends over the region other than the absorption band of carbon dioxide and with an intensity of radiation that extends over the absorption band being significantly less than that in the interaction radiation path; and
e) determining a partial pressure of carbon dioxide in the skin of the patient using a signal from the first radiation detector and a signal from the second radiation detector.

According to another aspect, there is provided a computer program element controlling apparatus and/or system as previously described which, if the computer program element is executed by a processing unit, is adapted to perform the method steps as previously described.

There is also provided a computer readable medium having stored the computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
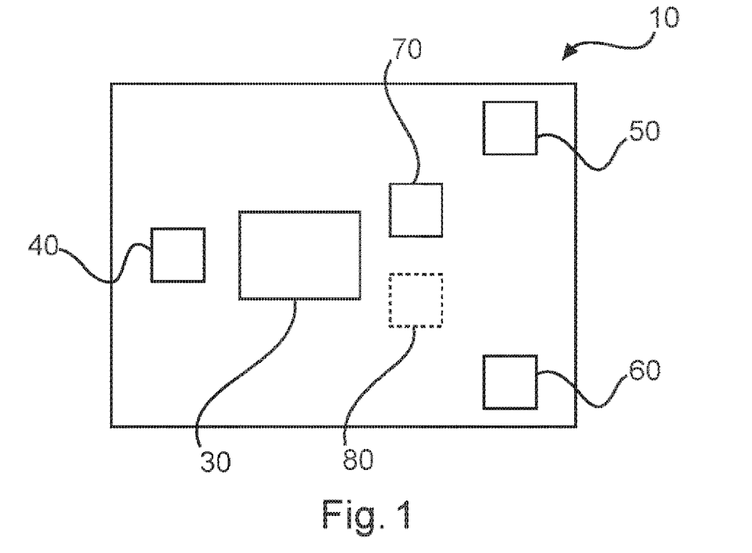
FIG. 1 shows a schematic set up of an example of an apparatus for the detection of carbon dioxide.

FIG. 1 shows an example of an apparatus 10 for the detection of carbon dioxide. The apparatus comprises a housing 20, a gas measuring chamber 30, a radiation source 40, a first radiation detector 50, a second radiation detector 60, and a radiation filter 70. The gas measuring chamber 30, the radiation source 40, the first radiation detector 50, the second radiation detector 60, and the radiation filter 70 are housed within the housing 20. A part of the housing 20 is configured to be placed in contact with a skin area of a patient. the part of the housing 20 and the gas measuring chamber 30 are configured such that gases diffusing through the skin area of the patient enter the gas measuring chamber 30. The gas measuring chamber 30 and radiation source 40 are configured such that at least some of the radiation emitted by the radiation source 40 enters the gas measuring chamber 30. The radiation entering the gas measuring chamber 30 has wavelengths that extend over an absorption band of carbon dioxide and has wavelengths that extend over a region other than the absorption band of carbon dioxide. The radiation filter 70 is positioned relative to the gas measuring chamber 30 such that an interaction radiation path is defined between the radiation source 40 through the gas measuring chamber 30 to the radiation filter 70. The first radiation detector 50 is positioned relative to the radiation filter 70 such that a first detection radiation path is defined that is in addition to the interaction radiation path. The second radiation detector 60 is positioned relative to the radiation filter 70 such that a second detection radiation path is defined that is in addition to the interaction radiation path. The radiation filter 70 is configured such that radiation in the first detection radiation path has wavelengths that extend over the absorption band of carbon dioxide and with an intensity of radiation that extends over the region other than the absorption band being significantly less than an intensity of radiation that extends over the region other than the absorption band in the interaction radiation path. The radiation filter 70 is configured such that radiation in the second detection radiation path has wavelengths that extend over the region other than the absorption band of carbon dioxide and with an intensity of radiation that extends over the absorption band being significantly less than an intensity of radiation that extends over the absorption band in the interaction radiation path. Signals from the first radiation detector 50 and second radiation detector 60 are useable to determine a partial pressure of carbon dioxide in the skin of the patient.

In an example, the gas measuring chamber has an inner surface coated with gold, silver, or aluminium or aluminium oxide. In this manner a maximum amount of radiation goes to the detectors.

In an example, the gas measuring chamber comprises a reflective tube.

In an example, the inner surface of the gas measuring chamber has a surface roughness less than the wavelength of the absorption band of carbon dioxide. In an example, the inner surface of the gas measuring chamber has a surface roughness less than half the wavelength of the absorption band of carbon dioxide. In an example, the inner surface of the gas measuring chamber has a surface roughness less than a quarter of the wavelength of the absorption band of carbon dioxide. In an example, the inner surface of the gas measuring chamber has a surface roughness less than an eight of the wavelength of the absorption band of carbon dioxide. In this way, scattering is reduced, leading to maximum amounts of radiation going to the detectors.

In an example, the radiation source acts as a gaseous seal to the gas measuring chamber. In this way, a further reduction in the necessary number of components is provided, leading to a further cost-effective solution in terms of intrinsic cost and assembly costs.

In an example, the radiation source is an LED.

In an example, the radiation source operates over the mid-infrared wavelength range. In an example, the radiation source operates over the infrared wavelength range. In an example, the radiation source operates over the visible wavelength range.

In an example, the radiation source produces the majority of its radiation extending over the wavelength range 3.8-4.5 µm.

In an example, the apparatus comprises at least one chimney in fluid communication with the gas measuring chamber and in fluid communication with the part of the housing configured to be placed in contact with the skin area of the patient. In this manner, gases diffusing through the skin of the patient can be transferred to the gas measuring chamber. The chimneys can be perpendicular to the gas measuring chamber, which enhances the efficiency of the gas measuring chamber.

In an example, a signal from the second radiation detector is useable to calibrate the radiation source. Thus, a feedback loop can be provided such that the source provides the same intensity of radiation into the gas measuring chamber.

In an example, a difference between a signal from the second radiation detector and from the first radiation detector is useable to calculate a partial pressure of carbon dioxide in the skin of the patient, In an example, the total volume of the gas measuring chamber is not greater than 2 µL. In an example, the total volume of the gas measuring chamber and the at least one chimney is not greater than 2 µL.

In an example, rather than operating for the detection of carbon dioxide, the apparatus in alternative arrangements can operate for the detection of $H_2O$ or anesthetic gases. The radiation filter would then be appropriately configured such that radiation in the first detection radiation path has wavelengths that extend over the absorption band of $H_2O$ (or the anesthetic gas) and with an intensity of radiation that extends over the region other than the absorption band being significantly less than that in the interaction radiation path and the radiation filter is configured such that radiation in the second detection radiation path has wavelengths that extend over the region other than the absorption band of $H_2O$ (or the anesthetic gas) and with an intensity of radiation that extends over the absorption band being significantly less than that in the interaction radiation path.

According to an example, the radiation filter is configured such that the second detection radiation path comprises radiation transmitted through the radiation filter, and the first detection radiation path comprises radiation reflected from the radiation filter.

In an example, the radiation filter comprises a reflectance passband that extends over the absorption band of carbon dioxide.

In an example, the centre wavelength of the reflectance passband is 4.26 micrometers.

In an example, a full width half maximum of the reflectance passband is 180 nanometers.

In an example, the apparatus comprises a second radiation filter, wherein the second radiation filter is configured such that the second detection radiation path comprises radiation transmitted through the second radiation filter.

In an example, the second radiation filter comprises a transmission passband centred at a wavelength centered where minimal gaseous absorption occurs.

In an example, the centre wavelength of the transmission passband is 3.91 micrometers. In an example, the centre wavelength of the transmission passband is 3.77 micrometers. In an example, the centre wavelength of the transmission passband is between 3.91 and 3.77 micrometers. In other words, a filter designed for 3.91 μm can be used at normal incidence to operate at 3.91 μm. however, that same filter can be angled, such that in effect the transmission passband shifts, where at an angle of 45 degrees the transmission passband can have shifted to 3.77 μm for the same filter. However, as long as no parasitic absorption occurs, reference data can still be effectively obtained. Thus, the skilled person can design, or have designed, appropriate interference filters to function at the desired orientation.

In an example, a full width half maximum of the transmission passband is 90 nanometers.

In an example, the radiation filter and second radiation filter are oriented parallel to each other.

Thus, a first filter can be a narrow pass band reflectance filter centred on a part of the spectrum where there is an absorption band of carbon dioxide, providing for a detection channel. The filter can have a broadband transmission profile that extends over a part of the spectrum where there is little absorption, providing for a reference channel that accounts for example for drift in the source output. In the reference channel, to further increase signal to noise in this channel and maximise dynamic range, a second narrowband transmission filter can be located that is centred on the part of the spectrum where there is little absorption. In this way, interference radiation filters can again be used to provide for detection and reference channels, but where the first filter has a narrowband reflectance profile rather than a narrowband.

According to an example, the radiation filter comprises a transmission passband centred at a wavelength where minimal gaseous absorption occurs.

According to an example, the centre wavelength of the transmission passband is 3.91 micrometers.

In an example, the centre wavelength can relate to different parasitic absorption bands.

According to an example, a full width half maximum of the transmission passband is 90 nanometers.

According to an example, the apparatus comprises a second radiation filter 80. The second radiation filter 80 is configured such that the first detection radiation path comprises radiation transmitted through the second radiation filter 80.

In an example, the second radiation filter is oriented at an angle of 45 degrees to the radiation filter. Thus, the second radiation filter and the second radiation detector placed behind the second radiation filter can be generally perpendicularly oriented to incident radiation. This means that there is a maximum available signal, and the interference filter can be selected as one that operates at 90 degrees, providing for a less expensive and accurate carbon dioxide detecting solution. The radiation filter and first radiation detector, that is in effect detecting a reference radiation channel, can then be oriented at 45 degrees to incident radiation. There is a loss in signal with respect to the maximum available signal because the radiation is now spread over an angle detector, but the radiation filter can be designed such that there is still a sufficient intensity of radiation being detected for this not to be problematic.

In an example, the radiation filter is oriented at an angle of 45 degrees to a central axis of the gas measuring chamber.

In an example, the apparatus comprises a prism situated at one end of the gas measuring chamber, and wherein the radiation filter is situated at a first surface of the prism, and the second radiation filter is situated at a second surface of the prism.

In an example, a third surface of the prism acts as a gaseous seal for gas measuring chamber. In this way, a further reduction in the necessary number of components is provided, leading to a further cost-effective solution in terms of intrinsic cost and assembly costs.

In an example, the prism is a sapphire prism.

In an example, at least one surface of the prism in addition to the first, second and third surfaces is coated with gold, silver or aluminium.

According to an example, the second radiation filter comprises a transmission passband that extends over the absorption band of carbon dioxide.

According to an example, the centre wavelength of the transmission passband is 4.26 micrometers.

According to an example, a full width half maximum of the transmission passband is 180 nanometers.

According to an example, the radiation filter acts as a gaseous seal to the gas measuring chamber. In this way, a further reduction in the necessary number of components is provided, leading to a further cost-effective solution in terms of intrinsic cost and assembly costs.

According to an example, the second radiation filter acts as a gaseous seal to the gas measuring chamber. In this way, a further reduction in the necessary number of components is provided, leading to a further cost-effective solution in terms of intrinsic cost and assembly costs.

As described above, the apparatus in different arrangements can detect $H_2O$ or anaesthetic gases rather than carbon dioxide, and the radiation filter and second radiation filter are configured appropriately—this the absorption band of carbon dioxide and the region other than the absorption band of carbon dioxide can refer to such spectral regions for H2O or anaesthetic gases.

Figure 2:
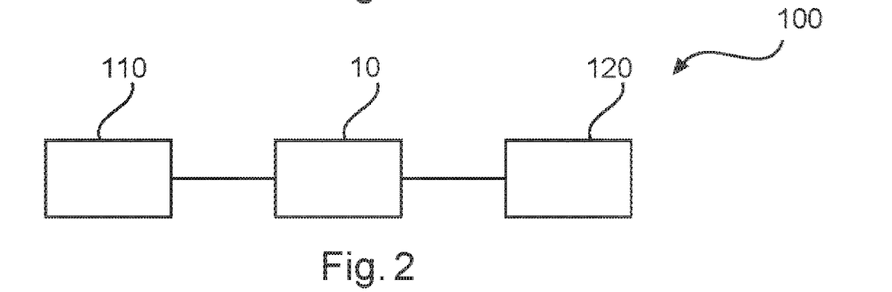
FIG. 2 shows a schematic set up of an example of a system for the detection of carbon dioxide.

FIG. 2 shows an example of a system 100 for the detection of carbon dioxide. The system 100 comprises an apparatus 10 for the detection of carbon dioxide as described above with respect to FIG. 1. The system also comprises a processing unit 110 and an output unit 120. The processing unit 110 is configured to control the apparatus 10, and is configured to control the output unit 120. The apparatus 10 is configured to provide the processing unit 110 with the signal from the first radiation detector and the signal from the second radiation detector. The processing unit 110 is configured to calculate the partial pressure of carbon dioxide in the skin of the patient. The calculation comprises utilization of the signal from the first radiation detector 50 and the signal from the second radiation detector 60. The output unit 120 is configured to output data representative of the partial pressure of carbon dioxide.

In an example, the calculation comprises a difference between the signal from the second radiation detector and the signal from the first radiation detector.

The system is calibration free during use, although an initial calibration before leaving the factory may still be required. It provides for ease of assembly, with a minimum number of components that can be off the shelf, and as such provides a cost-effective solution. It provides reliable results over long time periods of measuring the $CO_2$ concentration with a short response time because maximum amounts of available photons over required wavelength ranges are used both in an active (carbon dioxide detecting channel) and in a reference (relatively non-absorbing and non-perturbed channel). Although the apparatus of the system may still have a membrane which may be changed from time to time, the complex re-membraning procedure known from the electrochemical sensors is avoided. The system is temperature stable, reliable in use and avoids the need of light guides as the light source is a build-in broad band light source, which furthermore is cheaper than a tuneable laser.

Figure 3:
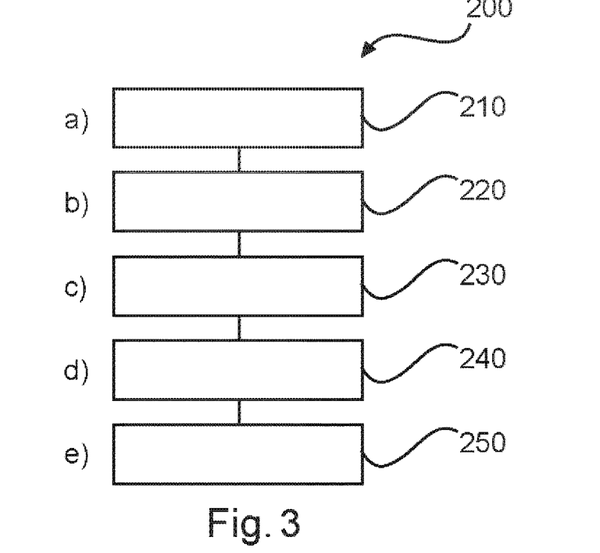
FIG. 3 shows a method for the detection of carbon dioxide.

FIG. 3 shows a method 200 for the detection of carbon dioxide in its basic steps. The method 200 comprises:

in a placing step 210, also referred to as step a), placing a part of a housing in contact with a skin area of a patient; wherein, the part of the housing and a gas measuring chamber within the housing are configured such that gases diffusing through the skin area of the patient enter the gas measuring chamber;

in an emitting step 220, also referred to as step b), emitting radiation from a radiation source within the housing. At least some of the radiation emitted by the radiation source enters the gas measuring chamber. The radiation entering the gas measuring chamber has wavelengths that extend over an absorption band of carbon dioxide and has wavelengths that extend over a region other than the absorption band of carbon dioxide;

in a positioning step 230, also referred to as step c), positioning a radiation filter relative to the gas measuring chamber such that an interaction radiation path is defined between the radiation source through the gas measuring chamber to the radiation filter;

in a positioning step 240, also referred to as step d), positioning a first radiation detector relative to the radiation filter such that a first detection radiation path is defined that is in addition to the interaction radiation path. Step d) also involves positioning a second radiation detector relative to the radiation filter such that a second detection radiation path is defined that is in addition to the interaction radiation path. The radiation filter is configured such that radiation in the first detection radiation path has a wavelength that extends over the absorption band of carbon dioxide and with an intensity of radiation that extends over the region other than the absorption band being significantly less than that in the interaction radiation path. The radiation filter is configured also such that radiation in the second detection radiation path has a wavelength that extends over the region other than the absorption band of carbon dioxide and with an intensity of radiation that extends over the absorption band being significantly less than that in the interaction radiation path; and in a determining step 250, also referred to as step e), determining a partial pressure of carbon dioxide in the skin of the patient using a signal from the first radiation detector and a signal from the second radiation detector.

In an example, forming the second detection radiation path comprises transmitting radiation through the radiation filter, and forming the first detection radiation path comprises reflecting radiation from the radiation filter.

In an example, the radiation filter comprises a transmission passband centred at a wavelength centred where minimal gaseous absorption occurs.

In an example, the centre wavelength of the transmission passband is 3.91 micrometers. In an example, a full width half maximum of the transmission passband is 90 nanometers.

In an example, the method comprises positioning a second radiation filter, and forming the first detection radiation path comprises transmitting radiation through the second radiation filter.

In an example, the second radiation filter comprises a transmission passband that extends over the absorption band of carbon dioxide.

In an example, the centre wavelength of the transmission passband is 4.26 micrometers. In an example, a full width half maximum of the transmission passband is 180 nanometers.

In an example, the radiation filter acts as a gaseous seal to the gas measuring chamber. In an example, the second radiation filter acts as a gaseous seal to the gas measuring chamber.

The apparatus, system and method for the detection of carbon dioxide are now described in more detail in conjunction with FIGS. 4-9.

Figure 4:
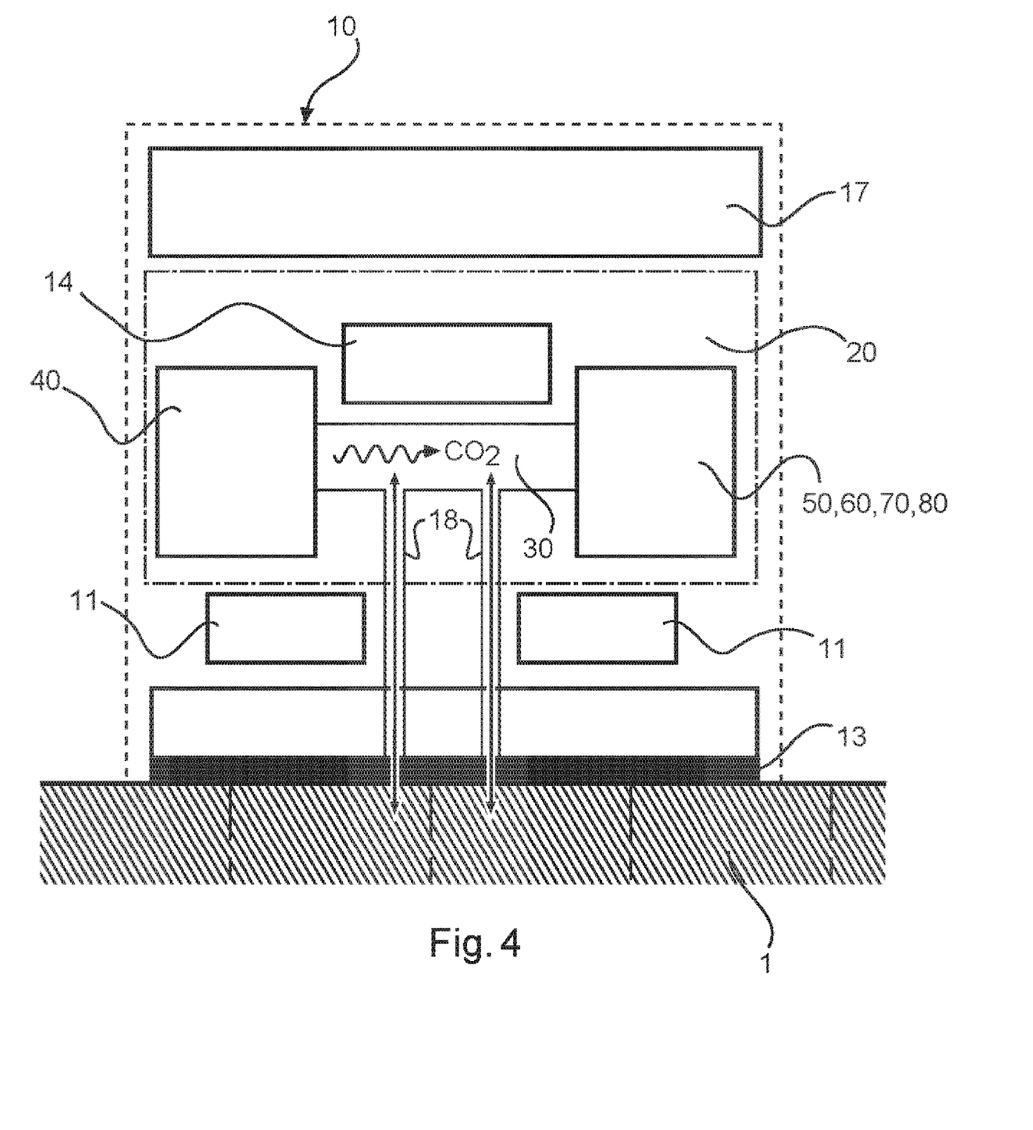
FIG. 4 shows a detailed schematic example of an apparatus for the detection of carbon dioxide.

FIG. 4 shows a detailed schematic block diagram of an example of an apparatus 10 for measuring the partial pressure of $CO_2$ in the skin 1 of a human patient. The apparatus 10 comprises a housing 10 shown as the outer dotted line, a gas measuring unit shown as the inner dotted. A part of the housing is a patient interface in the form of a membrane 13 contacting the skin 1 of the patient when in use. This membrane also serves to protect the apparatus against, for example, moisture and dust. The apparatus also comprises thermistors 11 for measuring the apparatus temperature, used for controlling a heating element 17. The temperature readout from the thermistors 11 is further used for signal processing when converting the detector signal into a partial pressure of $CO_2$ e.g. by the Severinghaus equation. The two chimneys 18 connect a gas measuring chamber 30 with the skin surface through the membrane 13, whereby gases diffusing through the skin are transported through the membrane 13 and the chimneys 18 to the measuring chamber 30. The measuring chamber is closed off at one end by a light source 40. The measuring chamber is closed off at the opposite end by a detector system that has a first radiation detector 50, a second radiation detector 60, a radiation filter 70 and a second radiation filter 80. The electronic board 14 comprises amplification, filtering. A/D converter, and signal processing means. The electronic board 14 communicates with the dual channel detector system, to convert the signals received from the first radiation detector 50 and the second radiation detector 60, into a value representing the partial pressure of blood gases in the skin of the patient. Furthermore the signal processing at the electronic board 14 receives information from at least one of the thermistors 11 regarding the apparatus 10 surface temperature to control the heating element 17 that heats the apparatus 10. Some functionality of the electronic board 14 can be undertaken by a processing unit 110 (not shown) that for example calculates the partial pressure of carbon dioxide, that is then output by an output unit 120 (not shown).

The heating element 17 is used to warm up the apparatus 10, which again warms up the skin of the human patient. The thermistors 11 are also used to control the heating element 17, to achieve the correct applied apparatus temperature and avoid burning the skin of the patient. The design as described with respect to FIG. 4 has two thermistors 11. One thermistor 11 would be enough for the purpose, however having two doubles the temperature control since it is important to measure the correct temperature for calculating the blood gas partial pressure and to avoid burning the skin of the patient. The heating of the apparatus 10 can be programmed by the hospital staff, defining measuring time and temperatures. The electronic board 14 also takes care of communication with external equipment (not shown), e.g. a monitor, controller unit connected via electrical cables or smart phones, computers, or tablets connected via wireless means such as WiFi, Bluetooth, GSM or like network. However, as discussed above some, or indeed all, of the functionality of the electronic board 14 can be carried out by processing unit 110.

The membrane 13 protects the internal parts of the apparatus 10, e.g. the electronics, the chimneys 18, and the gas measuring chamber 30 against intruding particles such as moisture and dust. The membrane 13 is permeable to blood gases, hydrophobic, mechanically robust and does not change the permeability or structural behavior when in contact with alcohol swab, contact gel or sweat. It allows the blood gases to diffuse from the patient skin to penetrate the membrane 13, while blocking dust and moisture from penetrating the membrane 13, which could potentially harm the apparatus 10, measuring parts, electronics, or block the chimneys 18 and thus obstructing the passageway for the blood gases between the skin of the patient and the gas measuring chamber 30.

Figure 6:
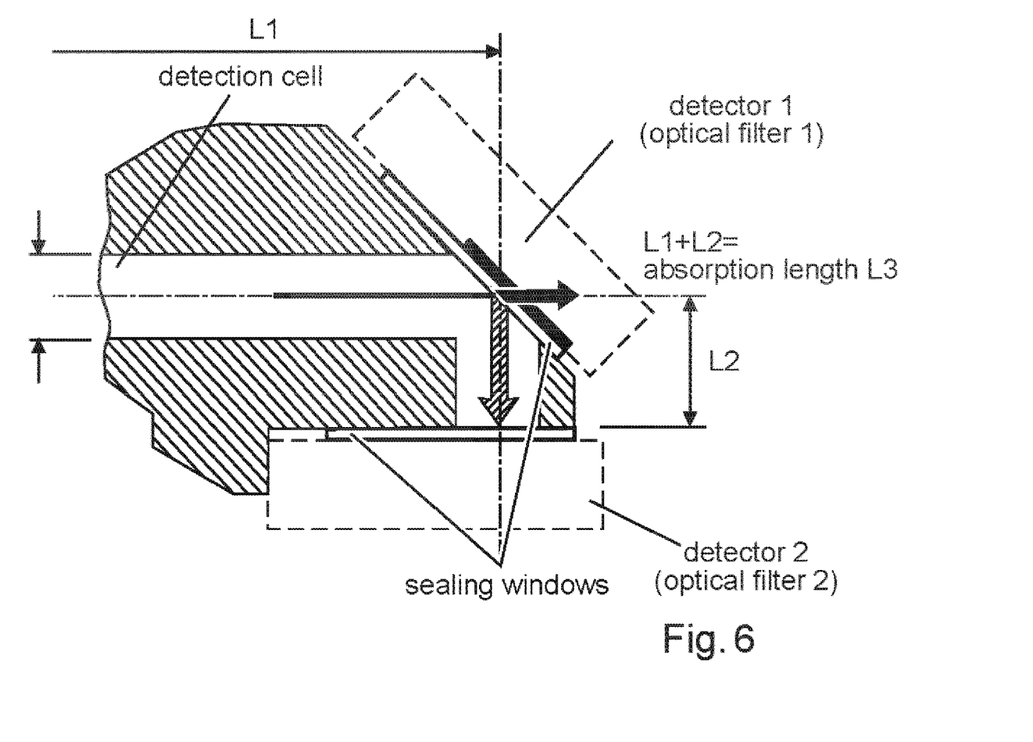
FIG. 6 shows a detailed schematic example of parts of an apparatus for the detection of carbon dioxide.

The chimneys 18 can have a diameter of 200 μm and can have a length of 4 mm or less. The length of the chimneys should preferably be as short as possible, since the volume of gas within the chimneys adds to the total volume of the gas measuring chamber 30, hence the volume here can have a negative effect on the sensitivity. Some length is however necessary to allow the photodetector and the light source to be positioned at either side of the gas measuring chamber 30, and allow the thermistors 11 to be fitted on the surface of the apparatus as they need to be close to the skin to detect the skin temperature. The diameter of the chimneys 18 also adds to the total volume and should be chosen as small as possible in order to keep the response time of the sensor low. On the other hand, larger diameter would decrease the risk of the chimneys 18 being blocked by intruding particles and would also allow a better flow of gas between the skin and the measuring chamber 23. Hence also here a diameter of 200 μm is a compromise. Two chimneys 18 have been chosen since one chimney may increase the risk of partly or fully blocking the chimney, whereas three or more chimneys 18 increase the total volume and the response time. The gas measuring chamber 30 has a total volume (here including the volume of the two chimneys 18) of no more than 2 μL. Due to the small volume of gas diffusing through the skin per time unit, a large volume would increase the response time of the apparatus 10, which should preferably be no more than one minute. Hence a volume of no more than 2 μL has been found to be a good compromise. The interaction length of the measuring chamber 30, i.e. the length of the measuring chamber 30 wherein the light may interact with the blood gas molecules is in the range of 1.5 mm to 30 mm. As shown in FIG. 6 a length of 7.5 mm has been used in one example of the apparatus.

Figure 5:
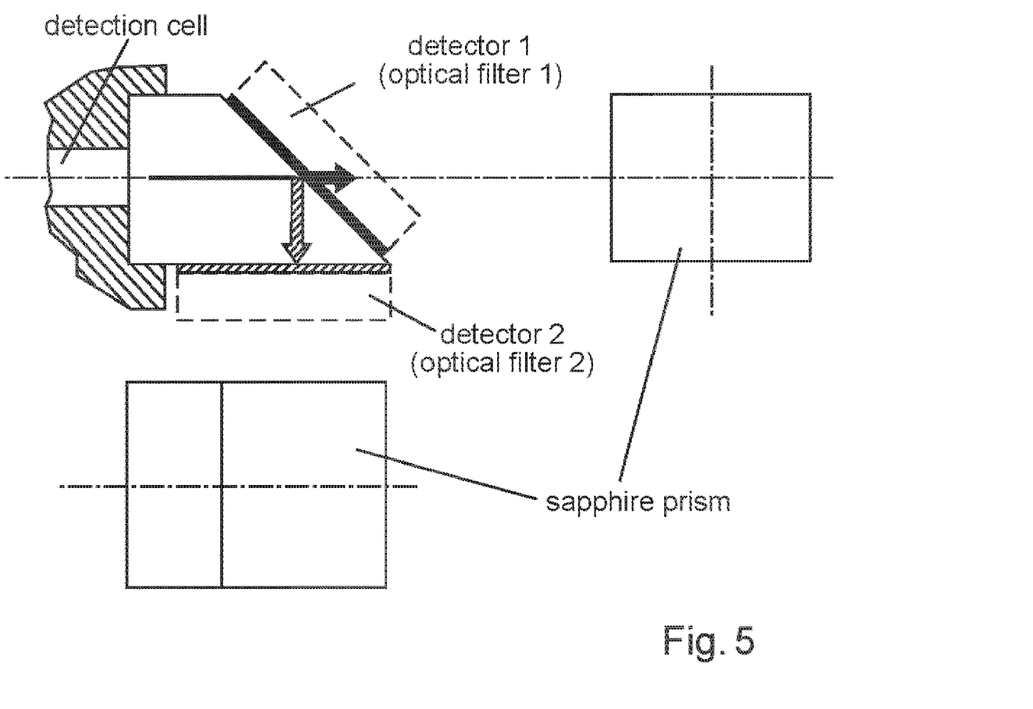
FIG. 5 shows a detailed schematic example of parts of an apparatus for the detection of carbon dioxide.

FIG. 5 shows a detailed example of parts of an apparatus for the detection of carbon dioxide. In this example a sapphire prism is used to provide a gaseous seal to the gas measuring chamber, here indicated as "detection cell". One interference filter detector pair is oriented at 45 degrees to the central axis of the gas measuring chamber. The interference filter is located on an output face of the sapphire prism. The radiation filter has a transmission passband located at a wavelength where there is minimal gaseous absorption, and reflects at other wavelengths. The reflected radiation propagates through the sapphire prism and is incident at 90 degrees to a second face of the sapphire prism. A second interference filter detector pair is located at this exit face of the sapphire prism. The interference filter has a transmission passband centred at an absorption band of carbon dioxide. Thus, the second interference filter and detector pair serves to detect carbon dioxide and because the filter is being used at 90° an off-the-shelf filter can be utilised thereby saving costs. At the same time, the first interference filter and detector pair serves as a reference channel providing information relating to the intensity of radiation propagating through the gas measuring chamber. The sapphire prism can have faces other than the input phase and the 2 output faces discussed above gold coated in order to maximise available radiation. In this arrangement, the interaction length of radiation propagating through the gas measuring chamber is exactly the same with respect to the reference channel and the detector channel. In the diagram optical filter is used to refer to the interference filter described above, and it is to be noted that a filter having a bandpass can actually be formed by a combination of two filters, one being a lowpass filter and a second being a highpass filter.

FIG. 6 shows a detailed example of parts of an apparatus for the detection of carbon dioxide, that is a slightly different arrangement to that shown in FIG. 5. In the arrangement shown in FIG. 6 the sapphire prism is not used, thereby leading to a cost saving, and the first and second filters themselves serve as gas tight seals for the gas measuring chamber. The interaction path length of radiation for the reference channel and the detector channel is then slightly different, but differs by unknown length, and therefore can be taken into account. The first radiation filter (interference filter) and second radiation filter (interference filter) and associated first and second detectors as shown in FIG. 6 are the same as that shown in FIG. 5.

In FIGS. 5-6 the first interference filter has a transmission band away from an absorbing feature but reflects over an absorption band of the gas to be detected, which in this case is carbon dioxide could be other gases if appropriate filters are designed. The second filter then has a transmission band located at an absorption band of the gas to be detected. However, the apparatus can operate in the opposite manner. Thus, the first radiation filter and detector conform the detector channel, through the first radiation filter having a narrow transmission band located over an absorption band of carbon dioxide and that reflects other radiation towards a second radiation filter. The second radiation filter can then have a narrow transmission band located at the region of the spectrum where there is little perturbation or absorption.

Figure 7:
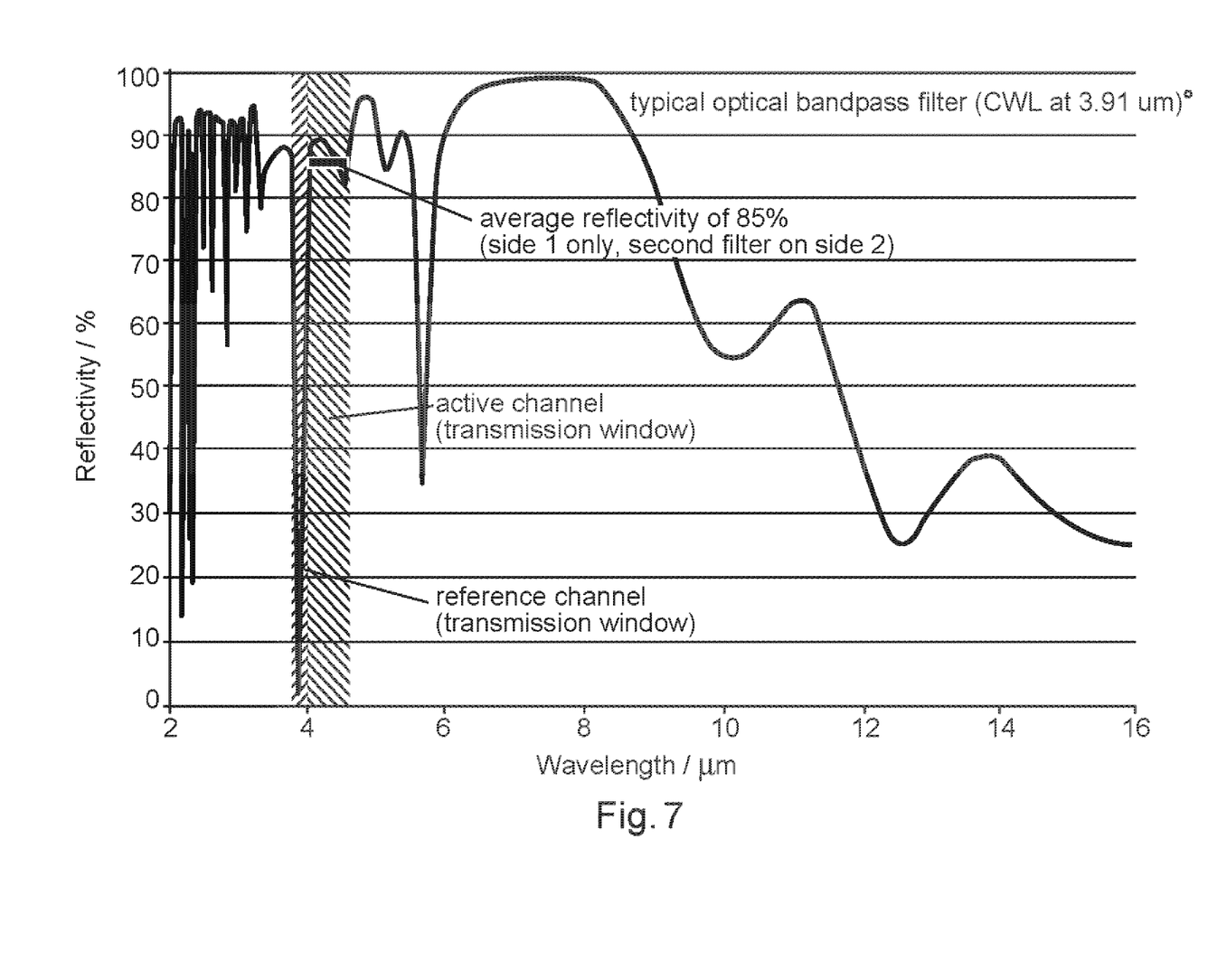
FIG. 7 shows active and reference transmissions windows for an example of the apparatus for the detection of carbon dioxide.

FIG. 7 shows a spectrum with the detector channel (active channel) and reference channel indicated over different parts of the spectrum for the apparatus described above.

Figure 8:
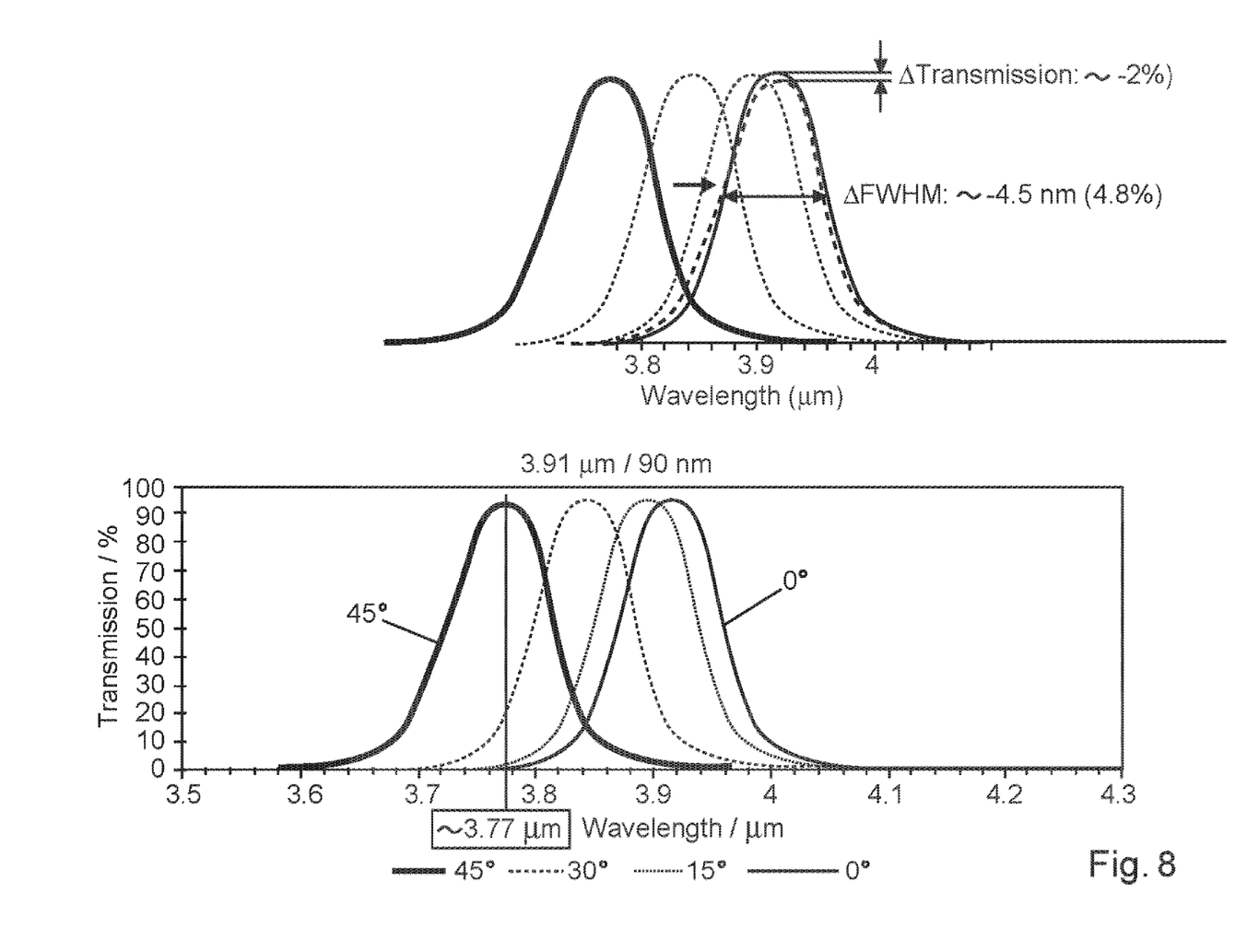
FIG. 8 shows the effect of tilting a radiation filter used in an example of the apparatus for the detection of carbon dioxide.
Figure 9:
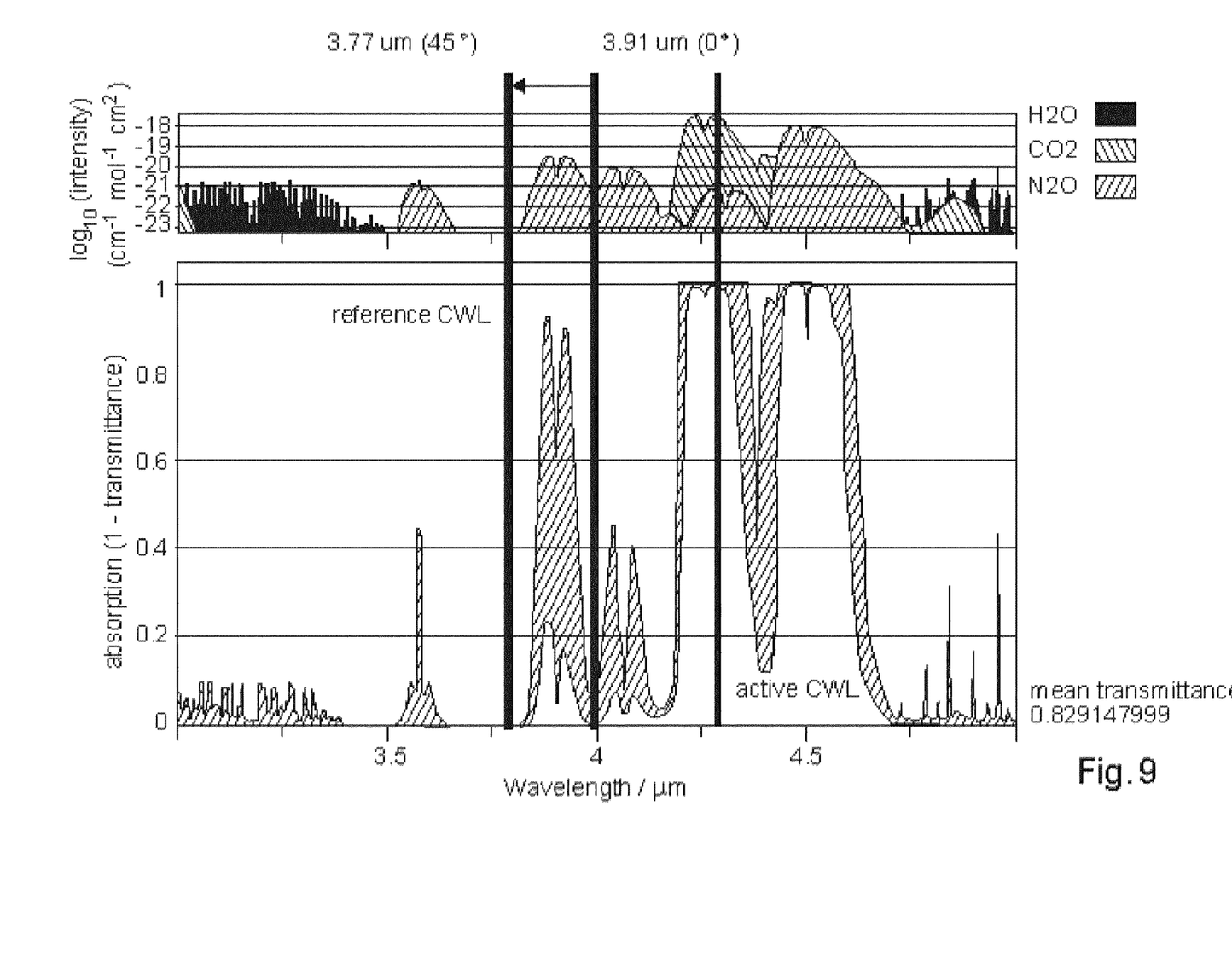
FIG. 9 shows the active and reference transmissions windows for an example of the apparatus for the detection of carbon dioxide for a filter, where a radiation filter on the reference channel has been tilted by 45 degrees.

As discussed above, it is important that the apparatus provide a cost effective solution for the detection of partial pressures of carbon dioxide of patients. Described apparatus has a minimal number of components, providing the ease of manufacture with non-stringent manufacturing tolerances being evident. Additionally, standard off-the-shelf interference filters can be used for the detector channel centred at 4.26 μm. The applicant has found that a standard off-the-shelf interference filter suitable for the reference channel has a passband centred at 3.91 μm. Tilting of the filter away from normal incidence however leads to a slight shift in the transmission passband. This is shown in FIGS. 8 and 9 where such a filter is still applicable for use when tilted at an angle of 45° because, the resultant transmission passband at 3.77 μm is itself located at an appropriate non-perturbing and non-absorbing part of the spectrum. Thus, the present system also provides a cost-effective solution in terms of components themselves as well as assembly of those components.

In another exemplary embodiment, a computer program or computer program element is provided that is characterized by being configured to execute the method steps of the method according to one of the preceding embodiments, on an appropriate apparatus or system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplar embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for detection of carbon dioxide, comprising:
   (a) a housing;
   (b) a gas measuring chamber;
   (c) a radiation source configured to emit radiation;
   (d) a first radiation detector;
   (e) a second radiation detector; and
   (f) a radiation filter;
   wherein, the gas measuring chamber, the radiation source, the first radiation detector, the second radiation detector, and the radiation filter are housed within the housing;
   wherein, a part of the housing is configured to be placed in contact with a skin area of a patient;
   wherein, the part of the housing and the gas measuring chamber are configured such that gases diffusing through the skin area of the patient enter the gas measuring chamber;
   wherein, the gas measuring chamber and radiation source are configured such that at least some of radiation emitted by the radiation source enters the gas measuring chamber, and wherein the radiation entering the gas measuring chamber has wavelengths that extend over an absorption band of carbon dioxide and has wavelengths that extend over a region other than the absorption band of carbon dioxide;
   wherein, the radiation filter is positioned relative to the gas measuring chamber such that an interaction radiation path is defined between the radiation source through the gas measuring chamber to the radiation filter and wherein the radiation filter acts as a first gaseous seal to the gas measuring chamber;

wherein, the first radiation detector is positioned relative to the radiation filter such that a first detection radiation path is defined that is in addition to the interaction radiation path; and wherein the second radiation detector is positioned relative to the radiation filter such that a second detection radiation path is defined that is in addition to the interaction radiation path;

wherein the radiation filter is configured such that the second detection radiation path comprises radiation transmitted through the radiation filter, and the first detection radiation path comprises radiation reflected from the radiation filter to thereby extend from the radiation filter to the first radiation detector;

wherein the radiation filter is configured such that the radiation in the first detection radiation path has wavelengths that extend over the absorption band of carbon dioxide and with an intensity of radiation that extends over the region other than the absorption band being significantly less than that in the interaction radiation path;

wherein the radiation filter is configured such that the radiation in the second detection radiation path has wavelengths that extend over the region other than the absorption band of carbon dioxide and with an intensity of radiation that extends over the absorption band being significantly less than that in the interaction radiation path; and wherein signals from the first and second radiation detectors are useable to determine a partial pressure of carbon dioxide in the skin area of the patient.

2. The apparatus according to claim 1, wherein the radiation filter comprises a transmission passband centered at a wavelength where minimal gaseous absorption occurs.

3. The apparatus according to claim 2, wherein the transmission passband is centered at a wavelength of 3.91 micrometers.

4. The apparatus according to claim 2, wherein a full width half maximum of the transmission passband is 90 nanometers.

5. The apparatus according to claim 1, wherein the apparatus comprises a second radiation filter, wherein the second radiation filter is positioned such that the first detection radiation path extends through the second radiation filter.

6. The apparatus according to claim 5, wherein the second radiation filter comprises a transmission passband that extends over the absorption band of carbon dioxide.

7. The apparatus according to claim 6, wherein the transmission passband is centered at a wavelength of 4.26 micrometers.

8. The apparatus according to claim 6, wherein a full width half maximum of the transmission passband is 180 nanometers.

9. The apparatus according to claim 5, wherein the second radiation filter acts as a second gaseous seal to the gas measuring chamber.

10. A system for detection of carbon dioxide, comprising:
an apparatus for detection of carbon dioxide according to claim 1;
a processing unit; and
an output unit;
wherein, the processing unit is configured to control the apparatus, and is configured to control the output unit;
wherein, the apparatus is configured to provide the processing unit with the signal from the first radiation detector and the signal from the second radiation detector;
wherein, the processing unit is configured to calculate the partial pressure of carbon dioxide in the skin of the patient, the calculation comprising the signal from the first radiation detector and the signal from the second radiation detector;
wherein, the output unit is configured to output data representative of the partial pressure of carbon dioxide.

11. The apparatus according to claim 1, wherein the radiation filter is oriented at an angle of 45 degrees to a central axis of the gas measuring chamber.

12. The apparatus according to claim 11, wherein the radiation filter comprises a transmission passband centered at a wavelength of 3.77 micrometers.

13. A method for detection of carbon dioxide, comprising:
a) placing a part of a housing in contact with a skin area of a patient; wherein the part of the housing and a gas measuring chamber within the housing are configured such that gases diffusing through the skin area of the patient enter the gas measuring chamber;
b) emitting radiation from a radiation source within the housing, wherein at least some of the radiation emitted by the radiation source enters the gas measuring chamber, and wherein the radiation entering the gas measuring chamber has wavelengths that extend over an absorption band of carbon dioxide and has wavelengths that extend over a region other than the absorption band of carbon dioxide;
c) positioning a radiation filter relative to the gas measuring chamber such that an interaction radiation path is defined between the radiation source through the gas measuring chamber to the radiation filter and wherein the radiation filter acts as a gaseous seal to the gas measuring chamber to thereby prevent leaking of the gases inside of the gas measuring chamber;
d) positioning a first radiation detector relative to the radiation filter such that a first detection radiation path is defined that is in addition to the interaction radiation path; and wherein a second radiation detector is positioned relative to the radiation filter such that a second detection radiation path is defined that is in addition to the interaction radiation path; wherein the radiation filter is configured such that the second detection radiation path comprises radiation transmitted through the radiation filter, and the first detection radiation path comprises radiation reflected from the radiation filter; wherein the radiation filter is configured such that the radiation in the first detection radiation path has a wavelength that extends over the absorption band of carbon dioxide and with an intensity of radiation that extends over the region other than the absorption band being significantly less than that in the interaction radiation path; and wherein the radiation filter is configured such that the radiation in the second detection radiation path has a wavelength that extends over the region other than the absorption band of carbon dioxide and with an intensity of radiation that extends over the absorption band being significantly less than that in the interaction radiation path; and
e) determining a partial pressure of carbon dioxide in the skin area of the patient using a signal from the first radiation detector and a signal from the second radiation detector.

14. An apparatus for detection of carbon dioxide, the apparatus comprising:
a housing;
a gas measuring chamber;
a radiation source configured to emit radiation;

a first radiation detector;
a non-transitory computer readable medium comprising a computer program element;
a second radiation detector; and
a radiation filter;
wherein, the gas measuring chamber, the radiation source, the first radiation detector, the second radiation detector, and the radiation filter are housed within the housing;
wherein, a part of the housing is configured to be placed in contact with a skin area of a patient; wherein, the part of the housing and the gas measuring chamber are configured such that gases diffusing through the skin area of the patient enter the gas measuring chamber;
wherein, the gas measuring chamber and radiation source are configured such that at least some of radiation emitted by the radiation source enters the gas measuring chamber, and wherein the radiation entering the gas measuring chamber has wavelengths that extend over an absorption band of carbon dioxide and has wavelengths that extend over a region other than the absorption band of carbon dioxide;
wherein, the radiation filter is positioned relative to the gas measuring chamber such that an interaction radiation path is defined between the radiation source through the gas measuring chamber to the radiation filter and wherein the radiation filter acts as a gaseous seal to the gas measuring chamber;
wherein, the first radiation detector is positioned relative to the radiation filter such that a first detection radiation path is defined that is in addition to the interaction radiation path; and wherein the second radiation detector is positioned relative to the radiation filter such that a second detection radiation path is defined that is in addition to the interaction radiation path;
wherein the radiation filter is configured such that the second detection radiation path comprises radiation transmitted through the radiation filter, and the first detection radiation path comprises radiation reflected from the radiation filter;
wherein the radiation filter is configured such that radiation in the first detection radiation path has wavelengths that extend over the absorption band of carbon dioxide and with an intensity of radiation that extends over the region other than the absorption band being significantly less than that in the interaction radiation path;
wherein the radiation filter is configured such that radiation in the second detection radiation path has wavelengths that extend over the region other than the absorption band of carbon dioxide and with an intensity of radiation that extends over the absorption band being significantly less than that in the interaction radiation path;
wherein the computer program element is configured to use signals from the first and second radiation detectors are useable to determine a partial pressure of carbon dioxide in the skin area of the patient; and
wherein the computer program element, when executed by a processor, is configured to carry out the method of claim 13 when the method of claim 13 is performed using the apparatus.

15. A non-transitory computer program element configured to control a system for detection of carbon dioxide, the system comprising:
an apparatus for the detection of carbon dioxide, the apparatus comprising:
a housing;
a gas measuring chamber;
a radiation source configured to emit radiation;
a first radiation detector;
a second radiation detector; and
a radiation filter;
wherein, the gas measuring chamber, the radiation source, the first radiation detector, the second radiation detector, and the radiation filter are housed within the housing;
wherein, a part of the housing is configured to be placed in contact with a skin area of a patient; wherein, the part of the housing and the gas measuring chamber are configured such that gases diffusing through the skin area of the patient enter the gas measuring chamber;
wherein, the gas measuring chamber and radiation source are configured such that at least some of radiation emitted by the radiation source enters the gas measuring chamber, and wherein the radiation entering the gas measuring chamber has wavelengths that extend over an absorption band of carbon dioxide and has wavelengths that extend over a region other than the absorption band of carbon dioxide;
wherein, the radiation filter is positioned relative to the gas measuring chamber such that an interaction radiation path is defined between the radiation source through the gas measuring chamber to the radiation filter and wherein the radiation filter acts as a gaseous seal to the gas measuring chamber;
wherein, the first radiation detector is positioned relative to the radiation filter such that a first detection radiation path is defined that is in addition to the interaction radiation path; and wherein the second radiation detector is positioned relative to the radiation filter such that a second detection radiation path is defined that is in addition to the interaction radiation path;
wherein the radiation filter is configured such that the second detection radiation path comprises radiation transmitted through the radiation filter, and the first detection radiation path comprise radiation reflected from the radiation filter;
wherein the radiation filter is configured such that the radiation in the first detection radiation path has wavelengths that extend over the absorption band of carbon dioxide and with an intensity of radiation that extends over the region other than the absorption band being significantly less than that in the interaction radiation path;
wherein the radiation filter is configured such that the radiation in the second detection radiation path has wavelengths that extend over the region other than the absorption band of carbon dioxide and with an intensity of radiation that extends over the absorption band being significantly less than that in the interaction radiation path; and
wherein signals from the first and second radiation detectors are useable to determine a partial pressure of carbon dioxide in the skin area of the patient;
a processing unit; and
an output unit;
wherein, the processing unit is configured to control the apparatus, and is configured to control the output unit;
wherein, the apparatus is configured to provide the processing unit with the signal from the first radiation detector and the signal from the second radiation detector;

wherein, the processing unit is configured to calculate the partial pressure of carbon dioxide in the skin area of the patient, the calculation comprising the signal from the first radiation detector and the signal from the second radiation detector;

wherein, the output unit is configured to output data representative of the partial pressure of carbon dioxide, wherein the computer program element, when executed by the processing unit, is configured to carry out at least the determining step of the method of claim 13 when the method of claim 13 is performed using the apparatus.

16. An apparatus, comprising:
(a) a housing;
(b) a gas measuring chamber;
(c) a radiation source configured to emit radiation;
(d) a first radiation detector;
(e) a second radiation detector; and
(f) a radiation filter;

wherein, the gas measuring chamber, the radiation source, the first radiation detector, the second radiation detector, and the radiation filter are housed within the housing;

wherein, a part of the housing is configured to be placed in contact with a skin area of a patient; wherein, the part of the housing and the gas measuring chamber are configured such that gases diffusing through the skin area of the patient enter the gas measuring chamber;

wherein, the gas measuring chamber and radiation source are configured such that at least some of radiation emitted by the radiation source enters the gas measuring chamber, and wherein the radiation entering the gas measuring chamber has wavelengths that extend over an absorption band of carbon dioxide and has wavelengths that extend over a region other than the absorption band of carbon dioxide;

wherein, the radiation filter is positioned relative to the gas measuring chamber such that an interaction radiation path is defined between the radiation source through the gas measuring chamber to the radiation filter;

wherein, the first radiation detector is positioned relative to the radiation filter such that a first detection radiation path is defined that is in addition to the interaction radiation path; and wherein the second radiation detector is positioned relative to the radiation filter such that a second detection radiation path is defined that is in addition to the interaction radiation path such that the second detection radiation path is colinear with the interaction radiation path;

wherein the radiation filter is configured such that the second detection radiation path comprises radiation transmitted through the radiation filter, and the first detection radiation path comprises radiation reflected from the radiation filter to thereby extend from the radiation filter to first radiation detector;

wherein the radiation filter is configured such that the radiation in the first detection radiation path has wavelengths that extend over the absorption band of carbon dioxide and with an intensity of radiation that extends over the region other than the absorption band being significantly less than that in the interaction radiation path;

wherein the radiation filter is configured such that the radiation in the second detection radiation path has wavelengths that extend over the region other than the absorption band of carbon dioxide and with an intensity of radiation that extends over the absorption band being significantly less than that in the interaction radiation path; and wherein signals from the first and second radiation detectors are useable to determine a partial pressure of carbon dioxide in the skin area of the patient.

17. The apparatus of claim 16, wherein the radiation filter acts as a first gaseous seal to the gas measuring chamber to thereby be configured to prevent leaking of the gas measuring chamber.

18. The apparatus of claim 16, wherein the gas measuring chamber extends to the radiation filter.

19. The apparatus of claim 16, wherein the interaction radiation path defines an incident angle normal to a surface the radiation filter, wherein the first detection radiation path defines a reflected angle normal to the surface of the radiation filter, wherein the incident angle and the reflected angle are equal in magnitude.

20. The apparatus of claim 16, wherein the first detection radiation path defines a 90 degree angle from each of the interaction radiation path and the second detection radiation path.

* * * * *